United States Patent [19]

Frazer

[11] Patent Number: Plant 7,317

[45] Date of Patent: Sep. 4, 1990

[54] DIEFFENBACHIA PLANT NAMED GOLDEN SUNSET

[75] Inventor: Edwin J. Frazer, Brisbane, Australia

[73] Assignee: Hartman Plant Laboratories, Inc., Sebring, Fla.

[21] Appl. No.: 353,706

[22] Filed: May 18, 1989

[51] Int. Cl.[5] ..... A01H 5/00

[52] U.S. Cl. ..... Plt./88

[58] Field of Search ..... Plt./88

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Dieffenbachia plant named Golden Sunset having highly patterned green and yellow-green variegated leaves, relatively short and round leaves, excellent branching, fast growth habit, and flexible leaves.

1 Drawing Sheet

The present invention comprises a new and distinct cultivar of Dieffenbachia hybrida known by the cultivar name Golden Sunset.

The new cultivar is a product of a planned breeding program carried out by the inventor Edwin J. Frazer in Kenmore, Queensland, Australia. The cultivar was discovered by the inventor from the seedling progeny of a cross made by the inventor from cultivars which are unknown at this time. Asexual propagation by division and tissue culture was used to increase the number of plants for evaluation and has demonstrated the stability of the combination of characteristics of Golden Sunset from generation to generation.

The following observations, measurements and values describe plants grown in Palmdale, Fla. under greenhouse conditions which closely approximate those generally used in horticultural practice.

The following traits have been repeatedly observed and are determined to be basic characteristics of Golden Sunset, which in combination distinguish Golden Sunset from other dieffenbachia of the same general type, for example, *Diffenbachia amoena* Tropic Snow.

1. Golden Sunset is shorter and has rounder leaves than Tropic Snow.

2. Golden Sunset has leaves that are more highly patterned and more yellow than Tropic Snow.

3. Golden Sunset is faster growing and more highly branched than Tropic Snow.

4. Golden Sunset has very flexible leaves that can be bent double without injury to the leaves.

All color references below are measured against The Royal Horticultural Society colour chart. Colors are approximate as color depends on horticultural practices such as light level and fertilization rate, among others.

The drawing comprises a front perspective color photograph of Golden Sunset, with color being depicted as accurately as possible with illustrations of this type.

The photo illustrates a plant of Golden Sunset in an 8 inch pot approximately 48 to 52 weeks following growth from tissue culture under appropriate growing conditions. All measurements are based on the above parameters.

Origin: Seedling, unknown parentage.

Classification: Deiffenbachia hybrid, cv. Golden Sunset.

Propagation: Asexual production either by tissue culture or division.

Plant: Golden Sunset reaches approximately 24 cm. to 30 cm. from the soil surface to the junction of the petioles of the last two (2) unrolled leaves, and approximately 55 cm. to 65 cm. in width.

Stem:

*Growth Pattern.*—The stem is erect in growth and is approximately 2.3 cm. to 3.0 cm. in diameter five (5) cm. above the soil surface. Internode distance is approximately 2.8 cm. to 3.2 cm. three (3) cm. above the soil.

*Color.*—The stem is 143C in color.

Petiole: The following information is based on the 2nd expanded leaf from the apex.

*Growth pattern.*—The petiole has fleshy edges extending from the midrib that will be referred to as wings. The wings are approximately 11 mm. to 14 mm. wide one half (½) from the petiole base to the wing tip. The wings extend from the base of the petiole to within approximately 2.8 cm. to 3.2 cm. of the leaf base. The apex of the wings is emarginate. The petiole follows the stem axis but diverges from the axis approximately 2.8 cm. to 3.2 cm. from the leaf base, forming a horizontal distance from the edge of the stem to the leaf base of approximately 0.8 cm. to 1.2 cm.

*Dimensions.*—The petiole is curved its base to the base of the leaf. The petiole is approximately 8 mm. to 12 mm. in diameter one-half way between the top of the wing and the base of the leaf. The petiole is approximately 13.5 cm. to 14.5 cm. in length.

*Color.*—The petiole wings and mibrib are 143C blotched with 145D in color, the same color as the midrib.

Leaf:

*Growth pattern.*—The leaf is ovate with a cuspidate/aristate apex and an auriculate/truncate base. The margin is entire. The leaf is asymmetric, with the side of the leaf unrolling first having less surface area and fewer undulations on the leaf margin than the side unrolling last. The leaf is oriented nearly parallel to the stem axis at the time of full unrolling, changing to perpendicular to the stem axis as more leaves unroll above it. The midrib is straight over the length of the leaf, curving down near the tip of the leaf. The leaf blade curves down slightly from the midrib to the margin.

*Dimensions.*—For the pot size and growing time indicated, the largest leaf is approximately 33 cm. to 36 cm. long and approximately 23 cm. to 25 cm. wide. An average sized leaf is approximately 26 cm. to 28 cm. long and approximately 17 cm. to 19 cm. wide. The leaf is moderately thick.

*Midrib.*—The midrib is thick and prominent.

*Primary veins.*—The primary veins are sunken into the upper surface and protrude out of the under surface. The primary veins are the same color as the leaf tissue surrounding them.

*Color and pattern.*—There are numerous areas of the leaf where color is significant, particularly on the upper surface. Upper surface: New leaf: Areas of dark green: 139A. Midrib: 149D. Light variegated areas: 144D. Mature leaf: Areas of dark green: Darker than 136A Midrib: 145D. Light variegated areas: 143C. Old leaf: All areas become darker as the leaf ages. Lower surface: New leaf: Areas of dark green: Greener than 191A. Grayer than 137C. Midrib: 145D, sides 145B. Light variegated areas: 145C. Mature leaf: Areas of dark green: greener than 189A. Midrib: Greener than 144D, sides darker than 124C. Light variegated areas: Greener than 144D. Old leaf: All areas become darker as leaf ages.

Axillary breaks: There are approximately 1 to 4 axillary breaks with at least one (1) leaf expanded. Leaves will show color by the first leaf and will have true color and pattern by the second leaf.

Inflorescence: The inflorescence is typical of dieffenbachia and has no commercial significance.

Roots: Thick white roots with finer laterals.

General observations: Golden Sunset has more branches and holds its leaves closer to the stem than the comparison cultivar Tropic Snow, thereby giving Golden Sunset a more dense appearance. Golden Sunset has a more complex variegation than Tropic Snow and is not as white. The leaves are more flexible than Tropic Snow. In addition, Golden Sunset finishes faster than Tropic Snow.

I claim:

1. A new and distinct cultivar of Dieffenbachia plant named Golden Sunset, as illustrated and described.

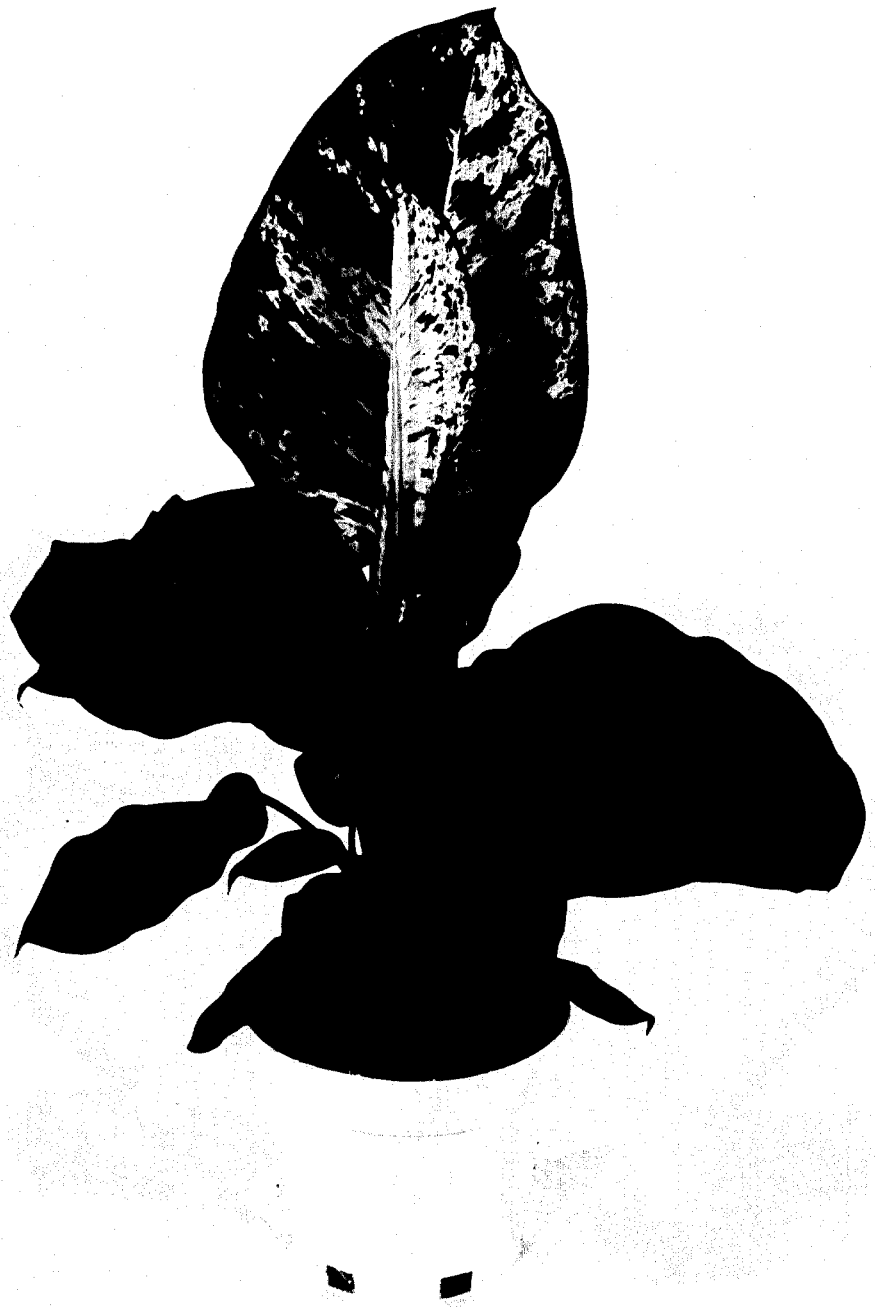

* * * * *